(12) United States Patent
Kuznicki et al.

(10) Patent No.: US 6,517,611 B1
(45) Date of Patent: Feb. 11, 2003

(54) OLEFIN SEPARATIONS EMPLOYING CTS MOLECULAR SIEVES

(75) Inventors: Steven M. Kuznicki, Whitehouse Station, NJ (US); Valerie A. Bell, Edison, NJ (US)

(73) Assignee: Engelhard Corporation, Iselin, NJ (US)

( * ) Notice: Subject to any disclaimer, the term of this patent is extended or adjusted under 35 U.S.C. 154(b) by 0 days.

(21) Appl. No.: 09/911,031

(22) Filed: Jul. 23, 2001

(51) Int. Cl.[7] ........................ B01D 53/047; B01D 53/22
(52) U.S. Cl. ........................ 95/144; 95/50; 95/96; 95/145; 585/818; 585/820
(58) Field of Search ............. 95/50, 96–106, 95/144, 145, 902; 585/818, 820

(56) References Cited

U.S. PATENT DOCUMENTS

| | | | | | |
|---|---|---|---|---|---|
| 3,717,572 | A | * | 2/1973 | De Gramont et al. | 95/144 X |
| 4,554,141 | A | * | 11/1985 | Scull et al. | 95/144 |
| 4,578,372 | A | * | 3/1986 | Hoving et al. | 502/74 |
| 4,655,798 | A | | 4/1987 | Ruch et al. | 55/64 |
| 4,699,892 | A | * | 10/1987 | Suzuki | 502/4 |
| 4,788,380 | A | * | 11/1988 | Lok et al. | 585/820 |
| 4,938,939 | A | * | 7/1990 | Kuznicki | 423/326 |
| 4,992,601 | A | * | 2/1991 | Kling | 95/144 X |
| 5,019,263 | A | * | 5/1991 | Haag et al. | 210/500.25 |
| 5,069,794 | A | * | 12/1991 | Haag et al. | 210/650 |
| 5,100,596 | A | * | 3/1992 | Haag et al. | 264/42 |
| 5,104,425 | A | * | 4/1992 | Rao et al. | 95/144 X |
| 5,107,058 | A | * | 4/1992 | Chen et al. | 585/818 |
| 5,110,478 | A | * | 5/1992 | Haag et al. | 210/650 |
| 5,245,099 | A | * | 9/1993 | Mitariten | 95/144 X |
| 5,346,535 | A | | 9/1994 | Kuznicki et al. | 95/96 |
| 5,453,263 | A | * | 9/1995 | Blooser et al. | 423/713 |
| 5,518,527 | A | * | 5/1996 | Tomizuka et al. | 95/144 X |
| 5,670,051 | A | * | 9/1997 | Pinnau et al. | 95/50 X |
| 5,744,687 | A | * | 4/1998 | Ramachandran et al. | 585/829 |
| 5,849,980 | A | * | 12/1998 | Lai | 95/144 X |
| 5,871,650 | A | * | 2/1999 | Lai et al. | 95/50 X |
| 5,989,316 | A | | 11/1999 | Kuznicki et al. | 95/130 |
| 6,051,517 | A | * | 4/2000 | Funke et al. | 502/4 |
| 6,068,682 | A | | 5/2000 | Kuznicki et al. | 95/130 |
| 6,124,517 | A | | 9/2000 | Kaminsky et al. | 585/829 |
| 6,200,366 | B1 | * | 3/2001 | Bulow et al. | 95/144 X |
| 6,293,999 | B1 | * | 9/2001 | Cheng et al. | 95/144 X |
| 6,296,688 | B1 | * | 10/2001 | Cheng et al. | 95/144 X |
| 6,315,816 | B1 | * | 11/2001 | Cho et al. | 95/144 X |
| 6,340,433 | B1 | * | 1/2002 | Kuznicki et al. | 210/651 |
| 6,387,159 | B1 | * | 5/2002 | Butwell et al. | 95/902 X |
| 6,395,067 | B1 | * | 5/2002 | Kuznicki et al. | 95/47 |
| 6,406,521 | B1 | * | 6/2002 | Cheng et al. | 95/144 X |

FOREIGN PATENT DOCUMENTS

| | | | | |
|---|---|---|---|---|
| JP | 48-013081 A | * | 4/1973 | 95/144 |

* cited by examiner

Primary Examiner—Robert H. Spitzer
(74) Attorney, Agent, or Firm—Russell G. Lindenfeldar

(57) ABSTRACT

Separation of ethylene from ethane is achieved by feeding a mixture of the $C_2$ hydrocarbons in contact with a CTS-1 crystalline titanium silicate molecular sieve which has a controlled pore size to selectively adsorb ethylene and size exclude ethane. The feed stream can also contain acetylene which can be selectively adsorbed from both ethane and ethylene by further controlling the pore size of the CTS-1 molecular sieve. Propane/propylene separation is also disclosed.

30 Claims, 1 Drawing Sheet

OLEFIN SEPARATIONS EMPLOYING CTS MOLECULAR SIEVES

FIELD OF THE INVENTION

This invention relates to use of adsorbents in purification of relatively impure olefins such as are typically produced by thermal cracking of suitable hydrocarbon feedstocks. More particularly, this invention concerns purification by passing an olefinic stream, containing alkanes, small amounts of acetylenic impurities, carbon oxides and/or other organic components, which are typically impurities in cracked gas oil, in contact with an adsorbent comprising a crystalline titanium silicate under conditions suitable for adsorption of olefins and/or alkynes.

Generally, this invention is directed to separating useful alkenes (olefins) and/or alkynes from alkanes (paraffins) of the same carbon content and is more specifically directed to separating ethylene or propylene from mixed streams of ethane/ethylene or propane/propylene, respectively, using CTS titanium silicate adsorbents.

BACKGROUND OF THE INVENTION

As is well-known, olefins, or alkenes, are a homologous series of hydrocarbon compounds characterized by having a double bond of four shared electrons between two carbon atoms. The simplest member of the series, ethylene, is the largest volume organic chemical produced today. Importantly, olefins including ethylene, propylene and smaller amounts of butadiene, are converted to a multitude of intermediate and end products on a large scale, mainly polymeric materials.

Commercial production of olefins is almost exclusively accomplished by pyrolysis of hydrocarbons in tubular reactor coils installed in externally fired heaters. Thermal cracking feedstocks include streams of ethane, propane or a hydrocarbon liquid ranging in boiling point from light straight-run gasoline through gas oil. Because of the very high temperatures employed, commercial olefin processes invariably coproduce significant amounts of acetylene. Required separation of the acetylene from the primary olefin can considerably increase the plant cost.

In a typical ethylene plant, the cracking represents about 25% of the cost of the unit, while the compression, heating, dehydration, recovery and refrigeration sections represent the remaining percentage of the total. This endothermic process is carried out in large pyrolysis furnaces with the expenditure of large quantities of heat, which is provided in part by burning the methane produced in the cracking process. After cracking, the reactor effluent is put through a series of separation steps involving cryogenic separation of products such as ethylene and propylene. The total energy requirements for the process are thus very large, and ways to reduce it are of substantial commercial interest. In addition, it is of significant interest to reduce the amounts of methane and heavy fuel oils produced in the cracking processor and utilize them for other than for their fuel value.

Hydrocarbon cracking is carried out using a feed, which is ethane, propane, or a hydrocarbon liquid ranging in boiling point from light straight-run gasoline through gas oil. Ethane, propane, liquid naphthas, or mixtures thereof are preferred feed to a hydrocarbon cracking unit. Hydrocarbon cracking is generally carried out thermally in the presence of a dilution steam in large cracking furnaces which are heated, at least in part, by burning methane and other waste gases from the olefins process resulting in large amounts of NO, pollutants. The hydrocarbon cracking process is very endothermic and requires large quantities of heat per pound of product. However, newer methods of processing hydrocarbons utilize, at least to some extent, catalytic processes, which are better able to be tuned to produce a particular product slate. The amount of steam used per pound of feed in the thermal process depends to some extent on the feed used and the product slate desired. Typically, steam pressures are in the range of about 30 lbs. per sq. in. to about 80 lbs. per sq. in. (psi), and amounts of steam used are in the range of about 0.2 lbs. of steam per pound of feed to 0.7 lbs. of steam per pound of feed. The temperature, pressure, and space velocity ranges used in thermal hydrocarbon cracking processes depend to some extent upon the feed used and the product slate desired, which are well-known and may be appreciated by one skilled in the art. The type of furnace used in the thermal cracking process is also well-known.

Several methods are known for separation of an organic gas containing unsaturated linkages from gaseous mixtures. These include, for instance, cryogenic distillation, liquid absorption, membrane separation and the so-called "pressure swing adsorption" in which adsorption occurs at a higher pressure than the pressure at which the adsorbent is regenerated. Cryogenic distillation and liquid absorption are common techniques for separation of carbon monoxide and alkenes from gaseous mixtures containing molecules of similar size, e.g. nitrogen or methane. However, both techniques have disadvantages such as high capital cost and high operating expenses. For example, liquid absorption techniques suffer from solvent loss and need a complex solvent make-up and recovery system.

Olefin-paraffin separations represent a class of most important and also most costly separations in the chemical and petrochemical industry. Cryogenic distillation has been used for over 60 years for these separations. They remain to be the most energy-intensive distillations because of the close relative volatilities. For example, ethane-ethylene separation ($c_2$ splitter) is carried out at about −25° C. and 320 lbs. per sq. in. gage pressure (psig) in a column containing over 100 trays, and propane-propylene separation is performed by an equally energy-intensive distillation at about −30° C. and 30 psig. The energy costs in olefin/paraffin separations are enormous. Recent revamps of ethylene plants have involved replacing distillation trays in the towers and heat exchange tubing in condensers and reboilers to reduce energy costs. New methods of process control and manipulation of feed point, product draw, de-ethanizer processing have all been used to control energy usages in an ethylene plant. Obviously, new methods of olefin/paraffin separation, which are less energy intensive as the present distillations, would be welcomed and could replace or at least augment the present $C_2$ splitter distillation processes.

Listed below are the mole weight and atmosphere boiling points for the light products from thermal cracking and some common compounds potentially found in an olefins unit. Included are some compounds, which have similar boiling temperatures to cracked products and may be present in feedstocks or produced in trace amounts during thermal cracking.

| Compound | Mole Weight | Normal Boiling Point, ° C. |
| --- | --- | --- |
| Hydrogen | 2.016 | −252.8 |
| Nitrogen | 28.013 | −195.8 |
| Carbon Monoxide | 28.010 | −191.5 |
| Oxygen | 31.999 | −183.0 |
| Methane | 16.043 | −161.5 |
| Ethylene | 28.054 | −103.8 |
| Ethane | 30.070 | −88.7 |
| Phosphine | 33.970 | −87.4 |
| Acetylene* | 26.038 | −84.0 |
| Carbon Dioxide* | 44.010 | −78.5 |
| Radon | 222.00 | −61.8 |
| Hydrogen Sulfide | 34.080 | −60.4 |
| Arsine | 77.910 | −55.0 |
| Carbonyl Sulfide | 60.070 | −50.3 |
| Propylene | 42.081 | −47.8 |
| Propane | 44.097 | −42.1 |
| Propadiene (PD) | 40.065 | −34.5 |
| Cyclo-Propane | 42.081 | −32.8 |
| Methyl Acetylene | 40.065 | −23.2 |
| Water | 18.015 | 100.0 |

*Sublimation temperature

Recently, the trend in the hydrocarbon processing industry is to reduce commercially acceptable levels of impurities in major olefin product streams, i.e., ethylene, propylene, and hydrogen. Need for purity improvements are directly related to increasing use of higher activity catalysts for production of polyethylene and polyproypropylene, and, to a limited, extent other olefin derivatives.

It is known that acetylene can be selectively hydrogenated and thereby removed from such product streams by passing the product stream over an acetylene hydrogenation catalyst in the presence of molecular hydrogen, $H_2$. However, these hydrogenation processes typically result in the deposition of carbonaceous residues or "green oil" on the catalyst, which deactivates the catalyst. Therefore, acetylene hydrogenation processes for treating liquid or liquefiable olefins and diolefins typically include an oxygenation step or a "burn" step to remove the deactivating carbonaceous residues from the catalyst, followed by a hydrogen reduction step to reactivate the hydrogenation catalyst. For example, see U.S. Pat. No. 3,755,488 to Johnson, et. al.; U.S. Pat. No. 3,792,981 to Hettick, et. al.; U.S. Pat. No. 3,812,057 to Morgan; and U.S. Pat. No. 4,425,255 to Toyoda. However, U.S. Pat. Nos. 3,912,789 and 5,332,705 state that by using selected hydrogenation catalysts containing palladium, at least partial regeneration can be accomplished using a hydrogenation step alone at high temperatures (600° to 700° F.) and in the absence of an oxygenation step.

Selective hydrogenation of the about 2,000 to 4,000 parts per million of acetylenic impurities to ethylene is generally a crucial operation for purification of olefins produced by thermal steam cracking. Typical of a small class of commercially useful catalysts are materials containing very low levels of an active metal supported on an inert carrier, for example, a particulate bed having less than about 0.03% (300 ppm) palladium supported on the surface skin of carrier pellets having surface area of less than about 10 $m^2$/gm.

Many commercial olefin plants using steam crackers use front-end acetylene converters, i.e. the hydrogenation unit is fed $C_3$ and lighter cracked gas, which feed has a high enough concentration of hydrogen to easily hydrogenate the acetylenic impurities; however, when run improperly, will also hydrogenate a large fraction of the ethylene and propylene product. Both hydrogenation of acetylene and ethylene are highly exothermic.

Accelerated catalyst deactivation and thermal runaways caused by loss in catalyst selectivity are common problems, which plague acetylene converters. Such problems result in unscheduled shutdowns and increased costs to replace deactivated catalyst.

The problem of over-hydrogenation is aggravated because the rate constant for ethylene hydrogenation to ethane is 100 times faster than for the hydrogenation of acetylene to ethylene. As a means to avoid a $C_2H_4$ hydrogenation thermal runaway, acetylene, carbon monoxide and diolefins concentrations must be high enough to cover most active sites so none are left to adsorb ethylene.

In certain instances, it may be useful to recover acetylene from the thermally cracked hydrocarbon stream since acetylene is a valuable raw material. Unfortunately, the boiling point of acetylene is close to the other $C_2$ hydrocarbons, ethane and ethylene, such that distillation is impractical. Liquid absorption of acetylene from a crude $C_2$-stream is disclosed in U.S. Pat. No. 4,655,798. In U.S. Pat. No. 6,124,517, acetylene impurities are adsorbed from an olefin stream by passing the feed stream such as obtained from thermal cracking through a particulate bed of adsorbent comprising a support material having high surface area on which is dispersed at least one metallic element in the zero valent state such as copper or silver. A high surface area gamma-aluminum silica, active carbon, clay and zeolites are disclosed as the support material. The adsorbent as disclosed in the patent is for removing acetylenic impurities from ethylene or propylene streams and is not described as useful for separating the desired olefins from the homogolous paraffins or in other words, separating ethylene from ethane and replacing the conventionally used $C_2$ splitter distillation process.

In commonly assigned U.S. Pat. No. 4,938,939, issued Jul. 3, 1990, Kuznicki disclosed a new family of synthetic, stable crystalline titanium silicate molecular sieve zeolites, which have a pore size of approximately 3–4 Angstrom units and a titania/silica mole ratio in the range of from 1.0 to 10. The entire content of U.S. Pat. No. 4,938,939 is herein incorporated by reference. Members of the family of titanium silicate molecular sieves, designated ETS-4, in the rare earth-exchanged form have a high degree of thermal stability of at least 450° C. or higher depending on cationic form. ETS zeolites are highly adsorptive toward molecules up to approximately 3–5 Angstroms in critical diameter, e.g. water, ammonia, hydrogen sulfide, $SO_2$, and n-hexane and are essentially non-adsorptive toward molecules, which are larger than 5 Angstroms in critical diameter.

The new family of microporous titanium silicates developed by the present assignee, and generically denoted as ETS, are constructed from fundamentally different building units than classical aluminosilicate zeolites. Instead of interlocked tetrahedral metal oxide units as in classical zeolites, the ETS materials are composed of interlocked octahedral chains and classical tetrahedral rings. In general, the chains consist of six oxygen-coordinated titanium octahedra and wherein the chains are connected three dimensionally via tetrahedral silicon oxide units or bridging titanosilicate units. The inherently different crystalline titanium silicate structures of these ETS materials have been shown to produce unusual and unexpected results when compared with the performance of aluminosilicate zeolite molecular sieves. For example, the counter-balancing cations of the crystalline titanium silicates are associated with the charged titania chains and not the uncharged rings, which form the bulk of the structure.

As synthesized, ETS-4 has an approximately 4 Å effective pore diameter. Reference to pore size or "effective pore diameter" defines the effective diameter of the largest gas molecules significantly adsorbed by the crystal. This may be significantly different from, but systematically related to, the crystallographic framework pore diameter. For ETS-4, the effective pore is defined by eight-membered rings formed from $TiO_6^{2-}$ octahedra and $SiO_4$ tetrahedra. This pore is analogous to the functional pore defined by the eight-membered tetrahedral metal oxide rings in traditional small-pored zeolite molecular sieves.

The pores of ETS-4 formed by the eight-membered polyhedral $TiO_6$ and $SiO_4$ units are non-faulted in a singular direction, the b-direction, of the ETS crystal and, thus, fully penetrate the crystal, rendering the ETS-4 useful for molecular separations. Recently, however, researchers of the present assignee have discovered a new phenomenon with respect to ETS-4. In appropriate cation forms, the pores of ETS-4 can be made to systematically shrink from slightly larger than 4 Å to less than 3 Å during calcinations, while maintaining substantial sample crystallinity. These pores may be "frozen" at any intermediate size by ceasing thermal treatment at the appropriate point and returning to ambient temperature. These materials having controlled pore sizes are referred to as CTS-1 (contracted titanosilicate-1) and are described in commonly assigned U.S. Pat. No. 6,068,682, issued May 30, 2000 herein incorporated by reference in its entirety. Thus, ETS-4 may be systematically contracted under appropriate conditions to CTS-1 with a highly controllable pore size in the range of 3–4 Å. With this extreme control, molecules in this range may be separated by size, even if the sizes of the respective molecules are nearly identical. This profound change in adsorptive behavior is accompanied by systematic structural changes as evidenced by X-ray diffraction patterns and infrared spectroscopy. The systematic contraction of ETS-4 to CTS-1 to a highly controllable pore size has been named the Molecular Gate™ effect. This effect is leading to the development of separation of molecules differing in size by as little as 0.1 Angstrom, such as $N_2/O_2$ (3.6 and 3.5 Angstroms, respectively), $CH_4/N_2$ (3.8 and 3.6 Angstroms), or $CO/H_2$ (3.6 and 2.9 Angstroms). High pressure $N_2/CH_4$ separation systems are now being developed. In this latter system, pressure swing adsorption (PSA) is utilized to adsorb the nitrogen from the natural gas stream, and desorb the nitrogen from the titanium silicate molecular sieve. Besides the use of CTS-1 for size controlled adsorption, it is known that barium-exchanged ETS-4 has the ability to size discriminate molecules from each other. For example, U.S. Pat. No. 5,989,316, discloses the use of Ba-exchanged ETS-4 to separate nitrogen from methane. The entire content of U.S. Pat. No. 5,989,316 is incorporated herein by reference.

As disclosed in U.S. Pat. No. 6,068,682 the CTS-1 zeolites may be generated using increasing thermal treatments which systematically size-exclude ethane (about 3.6 to above 4 Å), methane (about 3.8 Å), argon (about 3.7. Å), $N_2$ (about 3.6 Å), $O_2$ (about 3.5 Å), carbon dioxide (about 3.3 Å) and water (about 2.7 Å). Except for argon these sizes are Lennard-Jones kinetic diameters from *Zeolite Molecular Sieves*, Donald W. Breck Publishng Company, Malabar, Fla., 1984, p. 636. This reference lists argon as 3.4 Å, but our size exclusion data repeatedly shows it behaves in a sieving system as being between 3.8 and 3.6 Å. Useful effective separations disclosed in the patent include nitrogen from methane, $O_2$ from argon, and $O_2$ from $N_2$. Each of these separations may represent the heart of a significant commercial process. Olefin/paraffin separations of hydrocarbons having the same carbon content, e.g. ethylene/ethane, are not expressly disclosed.

Separations of fluid mixtures (gases or liquids) by adsorption utilizing the ETS-type molecular sieves have been proposed in which the molecular sieve is utilized in the form of a bed, typically fixed, through which the mixture to be separated flows. Both pressure swing adsorption (PSA) and thermal swing adsorption (TSA) have been suggested to effect separation of one or more fluids from mixtures containing same. Recently, however, ETS-type molecular sieve membranes have been developed and used for molecular separation in both gas and liquid state. Copending, commonly assigned U.S. Ser. Nos. 09/663,827, now U.S. Pat. No. 6,395,067; U.S. Ser. No. 09/663,828, now U.S. Pat. No. 6,340,433; and U.S. Ser. No. 09/663,829, all filed Sep. 15, 2000, disclose ETS-type membrane preparations and uses.

Membranes formed from ETS-4 molecular sieve are particularly useful inasmuch as the pores of the ETS-4 membranes can be systematically contracted under thermal dehydration to form CTS-1-type materials as disclosed in U.S. Pat. No. 6,068,682. Under thermal dehydration, the pore size of ETS-4 can be systematically controlled from about 4 Å to 2.5 Å and sizes therebetween and frozen at the particular pore size by ending the thermal treatment and returning the molecular sieve to ambient temperature.

It is therefore a general object of the present invention to provide an improved process which overcomes the aforesaid problem of prior art methods for production of unsaturated hydrocarbons, e.g. olefins, from thermal cracking of hydrocarbon feedstocks, which olefin can be used for manufacture of polymeric materials using higher activity catalysts.

It is another object of the present invention to provide an improved process for the separation of olefins from paraffins of the same carbon number as an alternative method to the conventional low temperature, energy intensive distillations as are presently used.

It is a further object of the present invention to conduct olefin/paraffin separations to separate similar boiling hydrocarbons of the same carbon number utilizing a solid molecular sieve adsorbent which has controlled pore size.

It is another object of the present invention to provide ethylene/ethane separations utilizing unique titanium silicate solid adsorbents which have pore sizes which can be controlled from about 2.5 to 4.0 Å.

It is yet another object of the present invention to provide a novel method of separating $C_2$ hydrocarbons from each other utilizing a solid titanium silicate adsorbent having controlled pore size.

Other objects and advantages of the invention will become apparent upon reading the following detailed description and appended claims.

SUMMARY OF THE INVENTION

Economical processes are disclosed for the separation of unsaturated hydrocarbons, in particular, ethylene such as produced by thermal cracking of hydrocarbons. The processes of the present invention are for the purposes of replacing or at least augmenting prior art olefin/paraffin low temperature distillation processes which have very large operational energy costs. More specifically, the invention is directed to separating olefins from feed streams containing paraffins by passing a gaseous feed mixture containing the respective olefin and paraffin of same carbon number in contact with a titanium silicate molecular sieve, namely, ETS-4 which has been heat treated to CTS-1 of the desired pore size for the separation. The CTS-1 adsorbent can be in the form of a particulate bed wherein the olefin/paraffin separation is accomplished by pressure swing adsorption (PSA) or the CTS-1 molecular sieve can be in the form of a membrane in which the pore size selectively allows one of the components to pass through the membrane as product and the other to be retained as retentate.

In another aspect of the present invention, the separation of acetylenic components from a gas mixture of ethylene and/or propylene can be achieved by contacting the gas mixture with the titanium silicate CTS molecular sieve which has been heat treated to the desired pore size to achieve separation.

BRIEF DESCRIPTION OF THE FIGURES

The FIGURE is a graph plotting the sorption of ethylene ($C_2H_4$) and ethane ($C_2H_6$) for Sr-exchanged ETS-4 after calcination and formation of CTS-1.

DETAILED DESCRIPTION OF THE INVENTION

Figure 1:
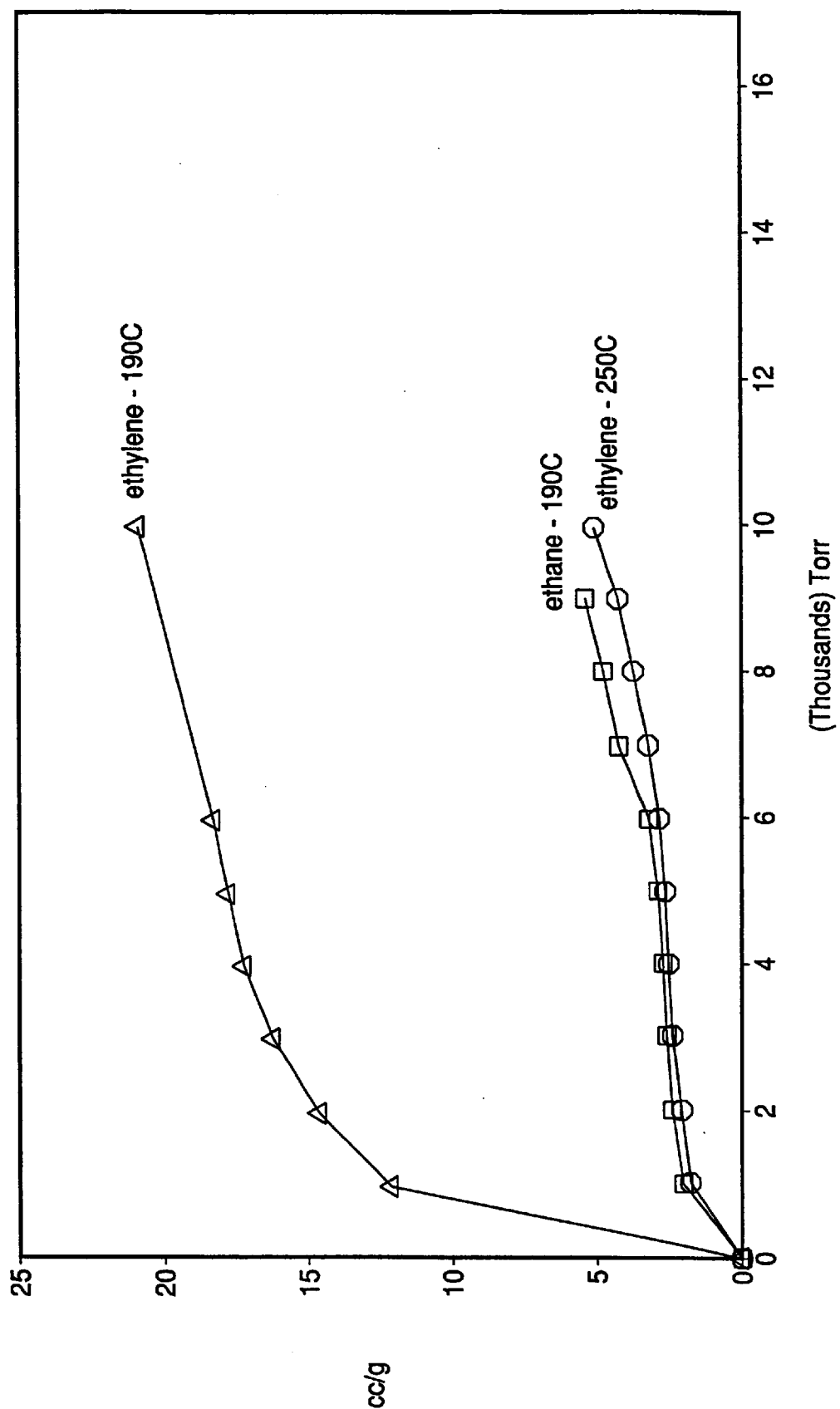

Processes of this invention are suitable for use in olefin/paraffin separations of feeds generally produced by thermal cracking of hydrocarbons.

Compounds of most interest with regard to separation by the method of the present invention have two to three carbon atoms, i.e., ethane, ethylene, acetylene, propane, propylene. For example, mixtures serving as a source of ethylene-containing feed for the process may contain about 1 to about 99 weight percent ethylene, about 1 to about 50 weight percent ethane, 0.1 to 5 wt. % acetylene and/or about 0 to about 50 weight percent methane. Typically, thermal cracked hydrocarbons are treated in demethanizers and deethanizers to separate $C_1$, $C_2$ and $C_3$ hydrocarbons from each other. It is to be understood other feed sources of $C_2$ and $C_3$ hydrocarbons can be treated in accordance with this invention, such as, for example, products from FCC and hydrocracking processes.

It is desirable to treat the gaseous mixture used in the process of the present invention to remove any gaseous hydrogen and/or carbon monoxide. The amount of hydrogen in the gaseous mixture should suitably be reduced to below 10 parts per million by weight, preferably below 2 parts per million by weight, and most preferably below 1 part per million by weight, prior to contact with the adsorbent Other polar gases such as hydrogen sulfide, metallic compounds should also be removed. Water may or may, not be removed prior to olefin/paraffin separation. The hydrogen and polar gaseous components can be removed by any known method. It is possible to combine the olefin/paraffin separation using CTS-1 with previous removal of the light and polar gases with a CTS-1 adsorbent which has been contracted from an ETS-4 adsorbent to a pore size which excludes the larger $C_2$ species. Aforementioned U.S. Pat. Nos. 6,068,682 and 6,395,067 describe use of the CTS-1 type adsorbents for removing polar gases from feed gas streams.

In preferred embodiments of processes according to the invention, the olefin in the gaseous mixture being separated is predominantly ethylene. The gaseous mixture typically contains up to about 40 wt. % ethane and up to about 5 wt. % acetylene, less than about 0.5 parts per million by volume of hydrogen and less than about 1 part per million by volume of mercury-containing, arsenic-containing, and sulfur-containing components, each calculated as the element. The gaseous mixture, while passing through the adsorbent, is at temperatures in a range upward of from about 0° C. to about 100° C., preferably in a range of from about 20° C. to about 65° C., and more preferably in a range of from about 25° C. to about 55° C. The temperature of adsorption must be. balanced with pore size and, consequently, the temperature of calcination of the ETS-4 into CTS. Thus, at higher adsorption temperatures, larger molecules may be adsorbed due to vibration of the pores. By using higher calcination temperatures, the pores can be effectively shrunk to counterbalance the increased pore vibration at elevated adsorption temperatures and provide the desired size exclusion.

As disclosed in commonly assigned U.S. Pat. No. 6,086, 682, it has been discovered that ETS-4 can be transformed into CTS-1 by the heating of ETS-4, preferably in the strontium or calcium form with or without low levels of sodium, at temperatures ranging from about 50° C. to 450° C., or preferably 200° C. to 350° C. for strontium and/or calcium mixed with sodium for 0.5 to 100 or more hours, preferably 24–48 hours, then cooling the thus treated material in order to lock in the desired pore size. The manner of cooling is not critical and it can be accomplished in air, vacuum or inert gas either slowly or rapidly. The calcination temperature used to achieve a desired pore diameter depends on the cations present in the reagent ETS-4. Although multivalent strontium and calcium are the preferred cations for CTS-1, other cations can be used with appropriate changes of temperature and duration of thermal treatment. Various combinations of Sr, Ca, Li, Mg, Na, H, Ba, Y, La, and/or Zn have all demonstrated separation selectivities. Zn-CTS-1 has shown particularly good separation selectivity. Additionally, the CTS-1 materials can be back-exchanged with metal, ammonium or hydrogen ions in a conventional manner if such is desired.

Also, useful in this invention may be barium-exchanged ETS-4 without pore contraction via calcination. This material is explicitly disclosed in aforementioned U.S. Pat. No. 5,989,316. The barium-exchanged ETS-4 of this invention is prepared by contacting ETS-4 with an inorganic salt of barium in order to effect the desired exchange. Still further, ETS-4 exchanged with a mixture of multivalent cations, with or without barium is also useful. Non-limiting examples of such multivalent cations include Sr, Ca, Mg, and Zn.

The ETS-4 which is used as the starting material can be prepared in accordance with the teachings of U.S. Pat. No. 4,938,939 wherein the halide-containing reagents are used or it can be prepared from reaction mixtures which are free from halide containing reactants in a manner analogous to the preparations of ETS-10 set forth in U.S. Pat. No. 5,453,263, the entire disclosure of which is incorporated herein by reference.

The crystalline titanium molecular sieves hereafter referred to as CTS-1, have a pore size of about 3–4 Å and have a composition in terms of mole ratio of oxides as follows:

$$1.0 \pm 0.25 \ M_{2/n}O:TiO_2:ySiO_2:zH_2O$$

where M is at least 1 cation having a valence n, y is 1–10 and z is from 0–10 and more preferably 0–5, and characterized by an X-ray powder diffraction pattern having the lines and relative intensity set forth in Table 1 below.

TABLE 1

XRD POWDER PATTERN OF CTS-1
(0–40° 2 theta)

| SIGNIFICANT d-SPACING (ANGS.) | I/I$_0$ |
|---|---|
| 11.4 ± 0.25 | Very Strong |
| 6.6 ± 0.2 | Medium–Strong |
| 4.3 ± 0.15 | Medium–Strong |
| 3.3 ± 0.07 | Medium–Strong |
| 2.85 ± 0.07 | Medium–Strong | wherein very strong equals 100, medium-strong equals 15–80.

In order to assure that the characteristic XRD pattern set forth in Table 1 is obtained, it is preferred that care be taken to ensure that samples remain dry after activation and throughout analysis. This is because some samples are less stable to rehydration and may be affected by moisture in ambient air. In most cases, such precautions are unnecessary because samples, especially those samples of low alkali metal content rehydrate only very slowly, sometimes over periods of years. A completely dry sample ensures that the proper XRD pattern will be obtained for both stable and metastable materials as such will be later defined. The above values and values later mentioned were collected using standard techniques on a Philips APD3720 diffractometer equipped with a theta compensator using an internal mica standard (SRM675). The theta compensator maintains a constant area of illumination on the sample, so X-ray intensities obtained from a theta compensated unit are not directly comparable to those of a non-compensated unit. Thus, all values mentioned in the specification and claims with regard to CTS-1 were determined by said theta compensated X-ray equipment. The radiation was the K-alpha doublet of copper, and a scintillation counter spectrometer was used. The peak heights, I, and the positions as a function of 2 times theta, where theta is the Bragg angle, were read from the spectrometer chart. From these, the relative intensities, 100I/I$_0$, where I$_0$ is the intensity of the strongest line or peak, and d (obs.), the interplanar spacing in A, corresponding to the recorded lines, were calculated.

It should be understood that this X-ray diffraction pattern is characteristic of all the species of CTS-1 compositions although it has been seen that in certain alkali metal cation forms of CTS-1, especially the pure sodium form, the 6.6±0.25 line becomes the most intense.

In accordance with the separation of this invention, the ETS-4 titanium silicate molecular sieve with the appropriate cation is calcined at a temperature which contracts the pores of the ETS-4 to the desired size so as to size-exclude the larger paraffin molecule from being adsorbed while at the same time providing adsorption of the olefin and/or acetylenic molecule. As previously said, it is believed that any one or a combination of cations can be substituted within the ETS-4 molecule and provide the necessary conversion to CTS-1 upon calcination. Strontium appears to be the preferred cation as well as a combination of sodium and strontium. Calcination of the ETS-4 to CTS-1 should be at a temperature of around 150–250° C. A high capacity and selectivity for ethylene over ethane for a Sr/Na-CTS-1 heated to 190° C. for 20 hours is shown in the example which follows. At a temperature of 250° C. calcination yielded a CTS molecular sieve which would not adsorb ethylene at 25° C. due to excess pore shrinkage. It is undoubtedly true, however, that complete separation can be obtained by precisely identifying the ideal contraction temperature and/or cation content. Again, while for the purpose of example in this application an Sr/Na-CTS material was chosen, it is believed that other cationic forms of CTS-1 may be applied to the olefin separation of this invention. In general, at least 50% of the exchange sites contain the desired cation, preferably 75–90% of the exchange sites include the desired cation.

It is somewhat surprising that Ba-exchanged ETS-4 or CTS-1 could be used for C$_2$ separation inasmuch as ethane, ethylene and acetylene all have at least one dimension which is equal to or greater than 4 Å, the maximum pore size of ETS-4. Thus, while the three dimensional sizes of the C$_2$ molecules vary depending on which reference source is consulted, in general, it is believed that the ethane molecule has a size which ranges from 3.6 to above 4 Å, ethylene from 3.1 to above 4 Å and acetylene from 3.1 to over 5 Å (rod-shaped). Yet regardless that the C$_2$ molecules have a size component which is greater than 4 Å, the CTS-1 titanium silicate can effectively separate the molecules by selective adsorption. It is also considered that separation of propylene from propane can be achieved by the present invention despite the large size of the respective molecules. Thus, propane with a size of 6.5 to 4.0 Å and propylene having a size of 6.2 to 4.0 Å would appear to be too large for the pore size of ETS-4 or CTS-1. However, by controlling the calcination temperature of the ETS-4, using the proper cations and using a high adsorption temperature, it is possible to selectively adsorb the smaller propylene from propane.

It may be desired to incorporate the crystalline titanium silicate CTS-1 with another material resistant to the temperatures and other conditions employed in separation processes. Such materials include inorganic materials such as clays, silica and/or metal oxides. The latter may be either naturally occurring or in the form of gelatinous precipitates or gels including mixtures of silica and metal oxides. Normally crystalline materials have been incorporated into naturally occurring clays, e.g., bentonite and kaolin, to improve the crush strength of the sorbent under commercial operating conditions. These materials, i.e., clays, oxides, etc., function as binders for the sorbent. It is desirable to provide a sorbent having good physical properties because in a commercial separation process, the zeolite is often subjected to rough handling which tends to break the sorbent down into powder-like materials which cause many problems in processing. These clay binders have been employed for the purpose of improving the strength of the sorbent.

Naturally occurring clays that can be composited with the crystalline titanium silicate described herein include the smectite, palygorskite and kaolin families, which families include the montmorillonites such as sub-bentonites, attapulgite and sepirotite and the kaolins in which the main constituent is halloysite, kaolinite, dickite, nacrite or anauxite. Such clays can be used in the raw state as originally mined or initially subjected to calcination, acid treatment or chemical modification. The relative proportions of finally divided crystalline metal titanium silicate and inorganic metal oxide can vary widely with the crystalline titanium silicate content ranging from about 1 to 99% by wt. and more usually in the range of about 80 to 90% by wt. of the composite.

In addition to the foregoing materials, the crystalline titanium silicate may be composited with matrix materials such as silica-alumina, silica-magnesia, silica-zironia, silica-thoria, silica-berylia, silica-titania as well as ternary compositions, such as silica-alumina-thoria, silica-alumina-zirconia, silica-alumina-magnesia and silica-magnesia-zirconia. The matrix can be in the form of a cogel.

The olefin separation of the present invention can be performed by virtually any known adsorption cycle such as pressure swing (PSA), thermal swing, displacement purge, or nonadsorbable purge (i.e., partial pressure reduction). However, the process of the present invention can be advantageously performed using a pressure swing cycle Pressure swing cycles are well known in the art.

The CTS-1 titanium silicate molecular sieves can also be produced as membranes by any technique known in the art, including methods known in the art for production of zeolite membranes. The membranes can be unsupported or supported on a porous metal or ceramic and the like. For example, the titanium silicate membranes can be formed from hydrothermal synthesis using aqueous solutions of the titanium silicate precursors spread against a substrate surface to form the membrane layer. Likewise, gels of the titanium silicate precursors can be spread across a surface and the gel precursors again heat treated to form the appropriate titanium silicate molecular sieve. Growth from solid precursors, such as shaped $TiO_2$ can be performed. Other methods include chemical vapor deposition which is also known in the art. Reference is made to aforementioned copending, commonly assigned U.S. Ser. No. 09/663,829, filed Sep. 15, 2000, which describes a method of forming titanium silicate membranes in-situ from shaped titania. Also, U.S. Pat. No. 6,051,517 which sets forth numerous articles describing the preparation of zeolite membranes as well as U.S. Pat. Nos. 5,110,478; 5,100,596; 5,069,794; 5,019,263; 4,578,372; 4,699,892, all of which describe zeolite membrane preparation and are incorporated herein by reference. For this invention, the particular membrane-forming method is not believed to be critical. Any method can be used so long as the membranes are relatively free of defects so as to prevent passage of retentate across the membrane.

The use of membranes to provide separation of the hydrocarbon mixtures could be an alternative to the use of beds of molecular sieves and use thereof in PSA or TSA processes. The membrane separation process is rather straightforward and does not require the time cycles of adsorption and desorption needed with lied bed molecular sieve technology. In membrane applications small molecules (permeate) are not adsorbed, but simply pass across the membrane of the membrane through distinctly sized pores. The larger sized molecules (retentate) cannot pass through the pores and are retained upstream of the membrane plane. Accordingly, in the process of the present invention, it is believed that membranes formed of the CTS-type titanium silicate molecular sieves, for example, would allow the diffusion of the ethylene and/or acetylene molecule, but retain the ethane as retentate. Specific operation of the separation of the olefin molecules by membrane separation is not an aspect of the present invention and it is understood that any known membrane processing scheme would be usable with the olefin separation of the present invention.

EXAMPLES

Example 1

Preparation of ETS-4

An alkaline titanium silicate gel was prepared. A sodium silicate solution was prepared using N-Brand (28 wt. % $SiO_2$, 9 wr. % $Na_2O$) and caustic (38 wt. % $Na_2O$) solutions. A separate titanic sulfate solution was prepared using titanic sulfate (10 wt. % $TiO_2$, 38 wt. % $H_2SO_4$), sulfuric acid, and deionized water. The sodium silicate and titanic sulfate solutions were mixed together using a high shear mixer forming a gel. The final pH of the undiluted gel was 11.5. Molar ratios of the gel composition are listed below. The gel was autoclaved at autogenous pressure in an unstirred Telfon lined vessel for 5 hours in an oven preheated to 230° C., then quenched in cold water. The white crystallized product was settled to the bottom of the autoclave liner under a clear supernatant liquid. The desired solid product was filtered and washed with deionized water to remove undesired salt byproducts, then dried at 115° C. for 1 hour at ambient pressure in air.

| Si/Ti | $H_2SO_4$/Ti | $Na_2O/H_2SO_4$ | moles Ti/1000 g gel |
|---|---|---|---|
| 3.00 | 3.474 | 1.371 | 0.220 |

Elemental analysis of the resultant crystalline ETS-4 produced the following results by X-Ray Fluorescence analysis:

| | wt. % |
|---|---|
| $SiO_2$ | 53.2 |
| $TiO_2$ | 27.0 |
| $Na_2O$ | 19.6 |
| $K_2O$ | 0.06 |

Example 2

Preparation of barium-exchanged ETS-4

The product from Example 1 was exchanged to the barium ETS-4 form using a ratio of 1 g NaETS-4:3 g $BaCl_2$:30 g $H_2O$, then washed with 90 g $H_2O$. This was repeated 2 more times per sample.

Elemental analysis of the above material produced the following results:

| | wt. % |
|---|---|
| $SiO_2$ | 43.4 |
| $TiO_2$ | 22.1 |
| BaO | 33.5 |
| $Na_2O$ | 0.44 |
| $K_2O$ | 0.06 |

As can be seen from the above Example, more than 95% of the original Na of the as-prepared ETS-4 of Example 1 was removed by this barium-exchange process.

The above material had an XRD pattern as set forth in Table 1 after heating overnight at 250° C. This pattern is representative of BaETS-4 materials in general.

TABLE 1

| d-spacings (Angstroms) | 100 $I/I_0$ |
|---|---|
| 11.43 | 100 |
| 8.47 | 3 |
| 6.71 | 9 |
| 5.77 | 4 |
| 5.22 | 6 |

TABLE 1-continued

| d-spacings (Angstroms) | 100 I/I$_0$ |
|---|---|
| 4.76 | 2 |
| 4.44 | 6 |
| 4.35 | 11 |
| 4.12 | 6 |
| 3.84 | 7 |
| 3.56 | 32 |
| 3.31 | 27 |
| 3.14 | 12 |
| 3.02 | 53 |
| 2.90 | 34 |
| 2.82 | 22 |
| 2.72 | 12 |
| 2.60 | 12 |
| 2.53 | 19 |
| 2.40 | 6 |

The above values and values later mentioned were collected using standard techniques on a Philips APD3720 diffractometer equipped with a theta compensator. The theta compensator maintains a constant area of illumination on the sample, so X-ray intensities obtained from a theta compensated unit are not directly comparable to those of a non-compensated unit. Thus, all values mentioned in the specification and claims with regard to barium ETS-4 were determined by said theta compensated X-ray equipment. The radiation was the K-alpha doublet of copper, and a scintillation counter spectrometer was used. The peak heights I, and the positions as a function of 2 times theta, where theta is the Bragg angle, were read from the spectrometer chart. From these, the relative intensities, 100 I/I$_0$, where I$_0$ is the intensity of the strongest line or peak, and d(obs), the interplanar spacing in A, corresponding to the recorded lines, were calculated. It should be understood that this powder X-ray diffraction pattern is typical of barium ETS-4 compositions prepared over a wide range of compositions and treatment temperatures.

It is noted that the X-ray diffraction patterns set forth in Table 1 contain some differences from the X-ray diffraction patterns set forth in U.S. Pat. No. 4,938,939.

It might very well be that differences in relative intensity and shifts in interplanar spacing result from the replacement of a substantial portion of the original cations with barium.

Example 3

A strontium exchanged ETS-4 titanium silicate molecular sieve was formed as described in Example 1 and 2 of U.S. Pat. No. 6,068,682.

Inasmuch as water must be removed from a molecular sieve before it can be effectively employed as a sorbent, the strontium exchanged ETS-4 was dried externally under a nitrogen flow at 155° C. first for 24 hours at 2 liters/minute of N$_2$ and then for 48 hours at 1 liter/minute N$_2$. The CTS titanium silicate was then formed from the dried strontium exchanged ETS-4 on a VTI Corporation, volumetric isotherm instrument (high pressure adsorption) unit. The strontium exchanged ETS-4 samples were heated in vacuum in the unit at either 190° or 25° C. for 20 hours to convert the molecular sieve to a CTS material.

FIG. 1 plots the isothermic adsorption of ethylene on the CTS1 molecular sieves which were formed by calcining the ETS-4 at 190° C. and 250° C. for 20 hours. The data also illustrates the isothermic adsorption of ethane with the CTS-1 molecular sieve formed by calcination of the ETS-4 at 190° C. The isothermic data shown in FIG. 1 was obtained in a unit using common equilibrium adsorption procedures.

As can be seen, the CTS molecular sieve which was formed by calcination of the strontium exchanged ETS-4 at 190° C. selectively adsorbs ethylene. What this illustrates is that the CTS-1 molecular sieve can have a controlled pore size to allow adsorption of the ethylene while size-excluding the ethane molecule. Control of pore size, however, needs to be precise, as it can be seen that by calcining the strontium exchanged ETS-4 at 250° C., very little adsorption of the ethylene molecule is achieved. formed at the higher temperature is essentially equivalent to the adsorption rate of the ethane molecule on the CTS molecular sieve obtained from calcining the strontium exchanged ETS-4 at 190° C.

Once given the above disclosure, many other features, modifications, and improvements will become apparent to the skilled artisan. Such other features, modifications, and improvements are, therefore, considered to be a part of this invention, the scope of which is to be determined by the following claims.

We claim:

1. A method of separating an olefin from a gaseous mixture which further contains a paraffin having the same carbon content as said olefin comprising; passing said mixture in contact with an ETS-4 or a CTS-1 titanium silicate molecular sieve adsorbent to selectivity adsorb said olefin and size exclude said paraffin from the pores of said molecular sieve, recovering a product stream which has a higher concentration of said olefin than said mixture, said ETS-4 being exchanged with barium or a mixture of multivalent cations with or without barium.

2. The method of claim 1, wherein said CTS-1 titanium silicate is exchanged with strontium or zinc cations.

3. The method of claim 2, wherein said CTS-1 titanium silicate contains a mixture of sodium and strontium cations.

4. The method of claim 1, wherein said CTS-1 titanium silicate is derived from an ETS-4 titanium silicate which has been calcined at a temperature of between 150° and 250° C.

5. The method of claim 4, wherein said calcined ETS-4 has been calcined at a temperature of 190° C. for 20 hours.

6. The method of claim 1, wherein said CTS-1 titanium silicate is in the form of a particulate bed.

7. The method of claim 6, wherein said product stream is formed by a pressure swing adsorption process.

8. The method of claim 1, wherein said titanium silicate is in the form of a membrane and said olefin passes through pores of said adsorbent and across the plane of said membrane, said product stream being obtained downstream of said membrane.

9. The method of claim 1, wherein said mixture further includes acetylene and said product stream includes acetylene at a higher concentration than said mixture.

10. The method of claim 1, wherein said mixture is obtained by the thermal cracking of said paraffin.

11. The method of claim 1, wherein said mixture is obtained by the thermal cracking of a hydrocarbon liquid ranging in boiling point from light straight-run gasoline to gas oil.

12. The method of claim 1, wherein said olefin is ethylene and said paraffin is ethane.

13. The method of claim 1, wherein said olefin is propylene and said paraffin is propane.

14. A method of recovering an olefin from a hydrocarbon liquid stream containing a paraffin of the same carbon content as said olefin;

comprising: thermally cracking said hyrdrocarbon liquid stream to form a mixture of at least said paraffin and said olefin, passing said mixture in contact with an ETS-4 or CTS-1 titanium silicate molecular sieve adsorbent to selectively adsorb said olefin and size exclude said paraffin, recovering a product stream having an olefin content greater than said mixture, said ETS-4 being exchanged with barium or a mixture of multivalent cations with or without barium.

15. The method of claim 14, wherein said mixture from thermal cracking said liquid hydrocarbon stream contains $C_3$ hydrocarbons which are removed by distillation prior to contacting said mixture with said titanium silicate adsorbent.

16. The method of claim 14, wherein said titanium silicate molecular sieve is in the form of a particulate bed and said product stream is formed by pressure swing adsorption.

17. The method of claim 14, wherein said CTS-1 titanium silicate is exchanged with strontium or zinc cations.

18. The method of claim 17, wherein said strontium exchanged CTS-1 is derived from a strontium-exchanged ETS-4 titanium silicate which has been calcined at a temperature of from 150° to 250° C.

19. The method of claim 14, wherein said olefin is ethylene and said paraffin is ethane.

20. The method of claim 19, wherein said titanium silicate is in the form of a membrane and said olefin passes through pores of said adsorbent and across the plane of said membrane, said product stream being obtained downstream of said membrane.

21. The method of claim 20, wherein said titanium silicate is CTS-1.

22. The method of claim 14, wherein said olefin is propylene and said paraffin is propane.

23. The method of claim 22, wherein said titanium silicate is in the form of a membrane and said olefin passes through pores of said adsorbent and across the plane of said membrane, said product stream being obtained downstream of said membrane.

24. The method of claim 14, wherein said titanium silicate is in the form of a membrane and said olefin passes through pores of said adsorbent and across the plane of said membrane, said product stream being obtained downstream of said membrane.

25. The method of claim 24, wherein said titanium silicate is CTS-1.

26. The method of claim 14, wherein said titanium silicate is said ETS-4.

27. A method of separating acetylene from a feed stream comprising acetylene and one or both of ethane and ethylene, comprising passing said feed stream in contact with an ETS-4 or CTS-1 crystalline titanium silicate molecular sieve which has a pore size to size exclude ethane and ethylene and adsorb acetylene, recovering a product stream having a concentration of acetylene greater than said feed stream, said ETS-4 being exchanged with barium or a mixture of multivalent cations with or without barium.

28. The method of claim 27, wherein said molecular sieve is in the form of a particulate bed and said product stream is recovered by a pressure swing adsorption process.

29. The method of claim 27, wherein said CTS-1 titanium silicate is exchanged with strontium or zinc cations.

30. The method of claim 29, wherein said strontium exchanged CTS-1 is formed by calcination of a strontium exchanged ETS-4 titanium silicate at a temperature of from about 150° to 250° C.

* * * * *